United States Patent [19]

Gorinsky

[11] Patent Number: 5,569,456
[45] Date of Patent: Oct. 29, 1996

[54] BIOLOGICALLY ACTIVE RUPUNUNINES

[76] Inventor: Conrad Gorinsky, c/o North Parade Chambers, 75 Banbury Road, Oxford, OX2 6PE, England

[21] Appl. No.: 189,781
[22] Filed: Feb. 1, 1994
[51] Int. Cl.$^6$ .................. A61K 35/78; A61K 31/675
[52] U.S. Cl. .................. 424/195.1; 514/82; 514/281; 514/841; 514/895; 514/918
[58] Field of Search .................. 424/195.1; 514/82, 514/281, 841, 895, 918

[56] References Cited

U.S. PATENT DOCUMENTS 5,162,331  11/1992  Staub et al. .................. 514/281

OTHER PUBLICATIONS

Cava et al. *J. Org. Chem.*, vol. 39(24), pp. 3588–3590, (1974).
Tackie et al. *Phytochemistry*, vol. 19(8), pp. 1882–1883, (1980).
Berthou et al. *Tetrahedron*, vol. 44(8), pp. 2193–2201, (1988).
Marshall et al. *Antimicrob. Agents Chemother.* vol. 38(1), pp. 96–103, (1994 Jan.).
Tetrahedron Letters No. 27, 1975, Oxford GB pp. 2249–2252 Shamma et al "A controlled oxidaiton of bis-benzylisoquinolines".

J. of Organic Chemistry vol. 39, No. 24, 1974, Easton U.S. pp. 3588–3591 Cava et al "Phlebicine, a new biphanylbis-benzylisoquinoline alkaloid from Cremastosperma polyphlebum".

*Primary Examiner*—John Kight
*Assistant Examiner*—Howard C. Lee
*Attorney, Agent, or Firm*—Nixon & Vanderhye

[57]  ABSTRACT

A rupununine, either in purified form or a derivative in which one or both of the hydroxyl groups is substituted, the rupununine having the formula:

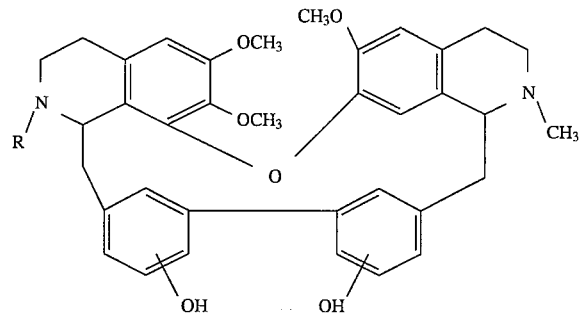

where R=—H or —CH$_3$.

2 Claims, No Drawings

BIOLOGICALLY ACTIVE RUPUNUNINES

The invention relates to alkaloids, and especially to bisbenzylisoquinoline alkaloids, and derivatives thereof.

It has been know for some time that Amerindian peoples of the Rupununi area of Guyana, South America chew the nuts of the greenheart tree (*Ocotea rodiaei*) as a crude form of contraception. Also, infusions of the bark of the greenheart tree have been used as a febrifuge and as an antiperiodic in fevers. Some bisbenzylisoquinoline alkaloids from other plants are known to have similar uses, and it was considered possible that the activity of the greenheart tree was attributable to a bisbenzylisoquinoline alkaloid. Although bisbenzylisoquinoline alkaloids have been extracted from the greenheart tree, no biological activity had previously been reported for such alkaloids.

We have now isolated an active bisbenzylisoquinoline alkaloid which we have named rupununine $C_{37}H_{40}O_6N_2$ which has now been characterized, as in Formula 1. The isolated compound has $OR_1$ and $OR_2$ one as a hydroxy group the other as a methoxy group, not distinguished in the mass spectrograph.

The structure of the rupununines of the invention is as follows:

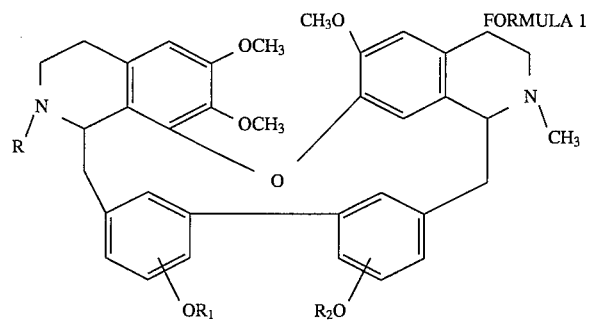

FORMULA 1 wherein R=—H or —CH$_3$, $R_1$ and $R_2$ are optional derivatisations the same or different and are thus for example —H, alkyl, especially —CH$_3$, acyl or glycosidyl. The nitrogens may of course be quaternized and in such form are regarded as within the above formulae.

Rupununine is a bisbenzylisoquinoline alkaloid. Related alkaloids not forming part of the invention, include tertiary alkaloids such as curine and isochondrodendrin. Many tertiary alkaloids of this series show biological properties. For example, thalicarpine (isolated from *Thalictrum dasycarpum*) is a hypotensive and cytotoxic agent. Cissampereine (isolated from *Cissampelos pareira*) exhibits cytotoxic action and tetrandrine (isolated from *Cyclea peltata*) is known to be a tumor-inhibitory alkaloid.

Although the greenheart tree (*Octotea rodiaei*) has been reported to be a source of d-curine, no biological activity has been reported of bisbenzylisoquinoline alkaloids from this plant. However it is known that among the Wapishana tribe of the Rupununi area of Guyana, the seeds (or fruits) of this tree have been used as a form of oral contraceptive. The fact that the alkaloids rodiasine, sepeerine, ocotine, ocotosine, demerarine, dirosine, norrodiasine and 2(+)-nortetrandrine have been isolated from the bark and seeds of this tree, brought speculation as to the possible biological properties existing in the plant.

The greenheart tree, *Octotea rodiaei*, is a large tree with a gently tapering erect stem, which reaches a height of approximately 60 to 90 feet and is branched only at the summit. The tree has a circumference of between 9 and 12 feet, and is recognised by its dense, glossy foliage and comparatively white flowers. The bark of the tree is smooth and whitish grey. The tree only grows in Guyana (formerly British Guiana), and speciments of the tree and its nuts may be found in the Herbarium at the Royal Botanic Gardens, Kew, England.

Ground defatted greenheart nuts may be extracted with for example, methanol, or isopropanol or with distilled water in an aspirator. The extract may then be reduced to a syrup for example, using a rotary evaporator, and the syrup was diluted and further extracted. Column chromatography may follow and the extract from the column further separated for example in a cascade partition chromatography solvent system. Counter-current distribution studies and Craig Distributions may then be carried out.

Crystals of rupununine have been isolated after preparative TLC and repeated recrystallization in e.g. acetone affords white needles which melt at between 214° and 217° C. The ultra violet spectrum of rupununine exhibits the characteristic absorption band at 283 nm corresponding to its aromatic chromophore (approximately 282 nm for most BBI's) with a second intense band at 206 nm. The molecular weight of rupununine where R is hydrogen, is approximately 608, and where R is methyl is approximately 622. The optical rotation $[\alpha]_D$ (CHCl$_3$), of rupununine is +257±10.

Infra-red spectroscopy reveals the presence of a doublet between 1500 to 1580 cm$^{-1}$ confirming that the alkaloid has a 1,2,3,4-tetrahydroisoquinoline base. The presence of a free hydroxyl is suggested by a weak singlet at about 3550 cm$^{-1}$.

The applicants conclude that this rupununine is responsible for certain of the effects traditionally seen following native use of extracts of the greenheart tree.

The present invention embraces the use of rupununine in the treatment of disease. For example, rupununine may be useful in the treatment of malaria, especially as a febrifuge and anti-periodic and in topical application for skin lesions. Rupununine is also through to be useful as a contraceptive or anti-fertility active, possibly with a role in the control of osetrus. This anti-fertility activity is probably highly selective for humans. Other applications of rupununine include a use as an inhibitor of soft tumor development, and possibly in the control of viruses such as AIDS and as an antimitotic through an antimetastic role or generally through a role in the cell proliferative process. Rupununine affects the neuropathways, and provides benefits in conditions that affect neurofunction, possibly as a treatment for intractable CNS disorders especially at a neurochemical level with GABA mediation. Its amphibatic properties suggest membrane action and an ability to pass cell barriers especially the blood brain barrier.

The present invention thus relates in general to the beneficial effects of rupununine in neurofunction.

Further uses envisaged are as a pesticide or preservative; especially for timber, nets or other materials in a marine environment or for example as an anti-fouling agent for boats and other structures, against barnacles, etc. The compound is applied to the pest or to a substrate affected by it or to be protected from it, or to a substrate to be preserved generally.

Derivatives of rupununine are envisaged, where the molecule of formula 1 is derived at $R_1$ and $R_2$. Suitable derivatives include those imparting polarity or lipohilicity to the molecule, for example to aid transfer of the molecule across cell membranes. A wide range of substituents is known, and selection may be from those acceptable in themselves and also in the sense of allowing the desirable properties of the free compound still to be shown.

Derivatives of rupununine according to the invention may include glycosides, alkyl derivatives, especially methyl, acyl derivatives, derivatives of essential fatty acids, such as gamma-linolenic acid and dihomo-gamma-linolenic acid and the other n-6 and n-3 essential fatty acids whether in the form of the acids or as the corresponding fatty alcohols.

The invention is further illustrated by the following example.

EXAMPLE

Methanol extraction

Ground nuts (2 kg) of *O. rodiaei*, defatted using petroleum ether $^{60}/_{80}$, were loosely packed into an aspirator (ca 5 liters), which was fitted with a tap plugged with cotton wool. This filter device retained the fine powdered particles during extraction with solvent. The vessel was then filled to the top with distilled methanol (2.5l), and left to soak overnight (16 hours) in a dark place. The methanol extract was then allowed to run off, effecting a continuous extraction until a total volume of 12 liters of extract was obtained. This was reduced to a dark syrup on the rotary evaporator under reduced pressure using a water pump, giving a syrupy methanol extract (200 g).

Distilled water (800 ml) was added to the concentrated syrup (180 g) to give a dark brown solution (pH=5). Ammonia (0.880, 2 ml.) was added to adjust the pH of the solution to a pH of about 8. The solution was then divided into two portions of approximately 450 ml. each.

The two portions were then shaken exhaustively with distilled chloroform (450 ml) portions in stoppered glass jars on a shaker for about 30 minutes.

The two layers obtained were separated with a separating funnel to give an orange-colored chloroform layer, and a thick brown aqueous layer. The partitioning with chloroform was repeated until the total volume of chloroform extract obtained was 3.5l.

The chloroform layer was dried over anhydrous sodium sulphate (40 g), filtered and evaporated to dryness on the rotary evaporator to give a brown syrup:chloroform extract (50.8 g, Fraction B), which was kept under nitrogen in the refrigerator until required. TLC using methanol:chloroform (1:10 v/v) indicated the presence of at least 5 alkaloidal components (detected by Dragendorff's reagent). The aqueous layer on drying gave a brown solid (95 g), and showed the presence of three alkaloidal substances by TLC using the same system as before.

Column chromatography of the chloroform extract (Fraction B),

A column (diameter 4 cm×length 77 cm) was packed using neutral alumina (60 g; Merck) as a slurry in chloroform (distilled). This was then equilibrated using the eluting solvent, distilled bench chloroform. The chloroform extract, Fraction B (50 g) was dissolved in the minimum amount of chloroform (50 ml), and loaded onto the column. The elution was carried out at 10 ml/min, and monitored by TLC.

Aliquots of 500 mls, of the eluted solvent were collected to give 3 main fractions which were quite well separated.

TABLE 1

|  | Aliquot No | Volume | Weight (Dried) |
|---|---|---|---|
| FRACTION B.1 | 1,2,3 | 1500 ml | 10 g |
| FRACTION B.2 | 4,5,6 | 1500 ml | 9 g |
| FRACTION B.3 | 7,8,9,10 | 2000 ml | 4 g |
| FRACTION B.4 (Methanol Fraction) | 11,12,13 | 1500 ml | 7 g |

TLC showed that fraction B.1 had the most alkaloidal content compared to the later fractions.

The solvent system was changed to pure methanol when very little alkaloidal substance seemed to be eluting through the column (monitored by TLC). The methanol fraction (Fraction B.4, 7 g) had similar Rf to fraction B.3. The dried fractions were pale yellow powders: and they were stored under nitrogen in the cold.

Partition chromatography: Cascade System

A solvent system consisting of $^{60}/_{80}$ petroleum ether:distilled water:distilled butanol (3:4:3 v/v) was prepared. This mixture was shaken and left to equilibrate at room temperature. The two phases separated out fairly easily within a minute. The upper phase (petrol layer) was distributed into five separating funnels so that each funnel had 100 ml., of solvent. The loser phase was treated likewise into another five separating funnels.

The chloroform extract (fraction B, 5.6 g) was dissolved in upper phase (100 ml) by shaking vigorously for 25 minutes on a shaker. The solution was then introduced into a separating funnel containing lower phase (100 ml.). The mixture was shaken well and left to equilibrate for five minutes. The two phases separated out during this time into a orange colored upper phase and a less colored lower phase. The upper and lower phases were then partitioned successively into the appropriate separating funnels prepared previously.

The procedure gave a separation of dark orange fraction in the upper phase and a paler fraction in the lower phase (butanol layer). TLC with methanol:chloroform (1:10 v/v) indicated that the upper phase (petrol layer) was richer in alkaloids (4 or 5 positive Dragendroff's spots), than the butanol layer (3 spots). After removal of solvent, the petrol layer (3.6 g) and butanol layer (1.5 g) gave dark brown solids and were stored under nitrogen in the fridge.

The experiment formed the basis of the Counter-current distribution studies and Craig distribution.

Counter-current distribution studies: Solvent system

A solvent system consisting of petroleum ether $^{60}/_{80}$ (distilled), distilled water and distilled butanol (3:4:3 v/v) was mixed in an aspirator (capacity 15.1) by stirring using an induction electric motor with a metal stirrer for four hours. The aspirator was kept covered to minimize evaporation of solvent, and later left to equilibrate in the Steady State Counter Current Distribution Machine (SSDM) room until used. The two phases were separated using a separating funnel (5 1). The solvents (15 1) were loaded into the two appropriate reservoirs (upper and lower phases) of the SSDM.

Solubility of Fraction B:

The sample used was Fraction B.1 (Chloroform extract). The solubility in upper phase solvent was found to be 0.5 g/ml. For the study it was possible to dissolve approximately 9 g in 25 ml., of upper phase solvent. This was done by vigorously shaking the sample 10 g) in the upper phase solvent (30 ml) for an hour, on a shaker, to dissolve the maximum amount of sample in the solvent.

A Craig Distribution was then attempted in order to determine the partition coefficient, K, of the various constituents of the chloroform extract, Fraction B.1. The extract (9 g) dissolved in 25 ml, of the upper phase was introduced into tube 0, and a Craig Distribution was set up using a 1:1 lower phase to upper phase program for 98 transfers. The SSDM was programmed to have a three minutes agitation time and 5 minutes settling time.

After 98 transfers were completed the train was analyzed by sampling a series of tubes (every 3rd tube), and their absorbances were determined at λ maximum 283 nm after appropriate dilution.

A TLC analysis was also attempted in the same manner (on the upper bank only; tubes no. +1 to +49). This was done after reducing the samples to a small volume (0.5 ml). An activated silica gel (60 G P254) plate of size 20 cm×20 cm was developed as in system TLC.1. The alkaloidal constituents were visualised using Dragendorff's reagent.

A distribution of the main fraction (Fraction C.1, 5.1 g) from tubes +46 to +41 was obtained which gave a Kp value of 15.33. TLC suggested 2 alkaloids of R.f.s 0.36 and 0.23. The contents of tubes +46 to +41 (Fraction C.1) were removed and the solvent removed. The rest of the train was also removed including another minor component of Kp 1.28 and solvent evaporated off.

TABLE 2

| TUBE NO. | FRACTION | PEAK TUBE | WEIGHT | PARTITION COEFFICIENTS Kp |
|---|---|---|---|---|
| +46 to +41 | C.1 | +43 | 5.09 g | 15.33 |
| +49 to +47 | C.2 | +46 | 0.73 g | 31.56 |
| +40 to +35 | C.3 | +40 | 0.63 g | 9.88 |
| +34 to +26 | C.4 | +26 | 0.04 g | 3.26 |
| +25 to +8 | C.5 | +19 | 0.03 g | 2.26 |
| +6 to 0 | C.6 | +6 | 0.08 g | 1.28 |
| −49 to −1 (LOWER BANK) | C.7 | −32 | 0.03 g | 0.21 |

The study showed that almost 80% of the sample moved to the right of the cell train with the upper phase (K value greater than 1). Hence the portions of interest in the SSDM train were tubes +46 to +41 (Fraction C.1).

Isolation of Rupununine—Preparative TLC:
Apparatus:

Long plates (1 m×20 cm) were coated with silica gel (60 G P254 Merck) and activated in a special one meter over overnight. The oven was also used for storing the plates after setting. The developing tank was a stainless steel lidded tank (1.10 cm×17 cm ×24 cm), and was lined with chromatography paper to ensure uniform vapor saturation on developing. A specially designed applicator or spreader was used to operate on a Shandon TLC spreader track when loading the sample. This device allowed the application of the dissolved sample as a streak on the coated plate, via an Agla syringe, on running the applicator down the length of the track.

The plates were developed with methanol:chloroform:diethylamine (14:85:1 v/v). The sample (Fraction C.1, 640 mg) was dissolved in distilled chloroform (4 ml), and applied onto the plates (using the spreader) as a streak: A loading of approximately 80 mg per plate gave a yield of about 40 mg., rupununine, and recover of about 78% of starting material. The developed plates were viewed under ultra violet light (λ 254 nm, 350 nm), and two distinct bands could be observed. These bands were both positive to Dragendorff's reagent.

The bands (Band I, Band II) (Rfs. 0.3, 0.4), were marked with a scribe, and scraped off the plate. The silica scrapings were then extracted with warm methanol leaching through the silica in a small column. The column was plugged tightly with cotton wool to trap the fine particles of silica. The solvent was removed on the rotary evaporator giving a pale yellow solid, rupununine (326 mg.) and O.R.II 176 mg.) Rupununine constituted about 0.16% of the original ground nuts of *O. rodiei* in weight.

Crystallization:

Rupununine (100 mg.) was dissolved in the minimum volume of distilled acetone (2 ml). The solution was warmed gently, filtered and then left in the refrigerator overnight. This produced white needles which were recrystallized in acetone giving crystalline rupununine (45 mg.). Further crystalline samples were also obtained by the same treatment with acetone, of Fraction C.1 and C.2. The crystals were dried in a drying pistol under nitrogen, over phosphorus pentoxide at 60° C. overnight. The crystalline white solid was fairly soluble in methanol, ethanol and chloroform, but only partially soluble in ether. The crystals melted between 214°–217° C., and were fairly stable, if kept under nitrogen at room temperature, even for prolonged periods.

Repeated recrystallization on the crystals produced identical needle-like crystals with constant melting point (214°–217° C.). Attempted recrystallisation in various other solvents, apart from acetone (such as ethanol, methanol, chloroform and ether) was unsuccessful.

Derivitzation is by procedures standard in themselves, for example:-

METHYLATION OF RUPUNUNINE USING DIAZOMETHANE

Experimental:

Dried, crystalline rupununine (200 mg) was dissolved in methanol (2 ml) and an ethereal solution was added in small portions until there was an excess of the reagent and left to stand at room temperature for five days. The excess diazomethane was removed by distillation. A pale yellow solid was obtained (208 mg) which melted between 127°–129° C. The reaction product was a mixture from which the methylated rupununine was isolated using preparative thin layer chromatography using silica gel (Merck 60 G p254) developed in methanol:chloroform (1:10 v/v).

Physical Data:

O-Methyl rupununine melted between 140°–145° C.

Chemical shifts (ζ) of the O-Methyl and N-Methyl protons in O-Methyl rupununine.

| O—Me | | | | N—Me | |
|---|---|---|---|---|---|
| 13 | 6 | 6' | 7 | 2' | 2 |
| 3.97 | 3.78 | 3.41 | 3.23 | 2.66 | — |
| 3.95 | 3.77 | 3.42 | 3.21 | 2.66 | — |

The Mass spectra yielded m/z 622 consistent with the expected methylation product of a 608 molecular weight compound with one free hydroxyl.

I claim:

1. A rupununine compound having the formula:

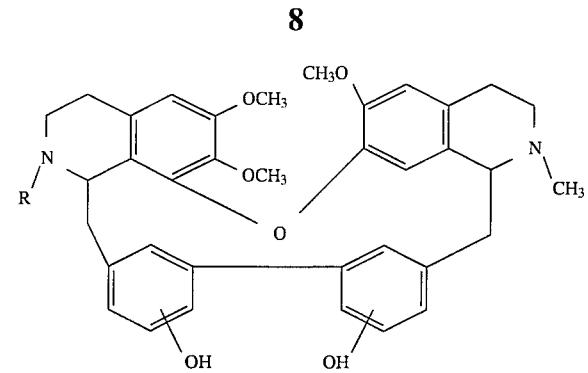

wherein R=—H or —CH$_3$.

2. A rupununine derivative having the formula:

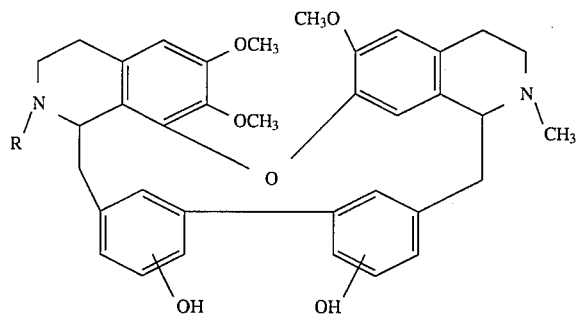

wherein R=—H or —CH$_3$ and one or both of the hydroxy groups is substituted with substituent other than alkyl and selected from the group consisting of fatty alcohol groups derived from the twelve natural n-6 or n-3 essential fatty acids, acyl groups and glycosidyl groups.

* * * * *